United States Patent [19]

Nicholas

[11] 4,320,344
[45] Mar. 16, 1982

[54] METAL-ALLOY THERMOELECTRIC CHARACTERISTIC ANALYZER

[76] Inventor: William R. Nicholas, 115 Linda La. Apt. #2, Palm Beach Shores, Singer Island, Fla. 33404

[21] Appl. No.: 80,224

[22] Filed: Oct. 1, 1979

Related U.S. Application Data

[63] Continuation-in-part of Ser. No. 927,736, Jul. 24, 1978, abandoned.

[51] Int. Cl.³ ............................................. G01N 25/18
[52] U.S. Cl. .................................... 324/451; 73/15 A
[58] Field of Search .............. 324/451; 73/15 A, 15 B

[56] References Cited

U.S. PATENT DOCUMENTS

| | | | |
|---|---|---|---|
| 2,330,599 | 9/1943 | Kuekni | 324/451 |
| 2,342,029 | 2/1944 | Zubko | 324/451 |
| 2,366,844 | 1/1945 | Doshek | 324/451 |
| 2,750,791 | 6/1956 | Hanysz et al. | 324/451 |
| 2,924,771 | 2/1960 | Greenberg et al. | 324/451 |
| 3,093,791 | 6/1963 | Richards | 324/451 |
| 3,667,032 | 5/1972 | Summers, Jr. | 324/451 |

OTHER PUBLICATIONS

Keem, "A Dynamic Seebeck Coefficient Measuring Devices", Chemical Instrunation 6(2), 1975, pp. 133-141.
"Tevotest 3.205" Institut Dr. Forester, Printed in West Germany 4.752.0 order no. 1-74222-527.

Primary Examiner—Gerard R. Strecker
Assistant Examiner—Walter E. Snow
Attorney, Agent, or Firm—Cushman, Darby & Cushman

[57] ABSTRACT

Apparatus for identifying the metal alloy composition of a test piece. Two thermoelectric probes are brought into contact with the test piece. Both of the probes are heated, one of which is heated to a predetermined temperature greater than the temperature of the other probe. The probes comprise electrodes of a thermally conductive material having in thermoelectric contact therewith, respective thermoelectric circuits having differing predetermined thermoelectric characteristics. A variable voltage divider electrically couples the respective thermoelectric circuits of the two probes. The output terminals of the voltage divider networks are connected in series opposition through a null meter or indicator which displays the test result. The voltage divider networks of the respective probes are mechanically or electrically slaved such that they are adjusted in synchronism, thereby desensitizing the apparatus to changes in test temperature, ambient temperature or the temperature of the respective test pieces. Further, simple calibration means are described and additionally, provisions for establishing further discriminants between alloys by (1) the use of different metal probe contact tips, (2) application of a magnetic field to encompass the probe/test piece junction, (3) momentarily varying the temperature of one of the electrodes through a Peltier effect, (4) generating biasing voltages across the probe/test junctions, and (5) comparing voltage-ampere ratio's of each alloy. One or a combination of such features may serve to alter and/or reveal thermoelectric characteristics for discriminating between alloys of similar chemical composition or to confirm the identity of known metal alloys or to establish positive identification of metals of unknown chemistry or to detect alloying segregation in high quality metal products.

26 Claims, 4 Drawing Figures

METAL-ALLOY THERMOELECTRIC CHARACTERISTIC ANALYZER

This application is a Continuation-In-Part of Ser. No. 927,736 filed July 24, 1978, now abandoned.

BACKGROUND OF THE INVENTION

The present invention relates to devices for identifying the metallic composition of a workpiece and more particularly to devices for identifying the metallic composition of a workpiece by measurement of its unique thermoelectric characteristics.

As is well know, when two dissimilar metals are joined in an electric circuit and the two metals are heated or maintained at different temperatures, an electromotive force (EMF) is developed in the circuit in accordance with the so called Seebeck effect. In general, the EMF generated is a function of the temperature and the chemical composition of the particular materials forming the junction.

The Seebeck effect has been utilized in non-invasive (non-destructive) testing of production lots of a specified alloy for quality assurance, for detecting alloys which inadvertently become mixed during a stage of a production process, and for identifying the metal or alloy composition of an unknown workpiece.

Descriptions of such devices are provided in the following U.S. Pat. Nos.: 2,330,599 (Kuehni, 1943); 2,342,029 (Zubko, 1944); 2,366,844 (Doschek, 1945); 2,750,791 (Hanysz et al., 1956); 2,924,771 (Greenberg et al., 1960); 3,093,791 (Richards, 1963); 3,667,032 (Summers Jr., 1972); and 4,156,849 (Rowsey, Snavely, Luce, 1979).

Another example of such a device is the Institut Dr. Forster Tevotest 3.205.

In general, such devices have not provided sufficient resolution and/or repeatable accuracy for distinguishing between alloys with similar compositions. Further, maintaining the test probe at a constant temperature has been critical. For example, the device described in the above noted Summers Jr. patent comprises first and second probes of identical metallic composition. One probe is heated so as to maintain a constant temperature that is elevated with respect to that of the second probe. The two probes are connected in series opposition such that the EMF developed by the cooler probe is subtracted from the higher EMF developed by the heated probe to produce a net EMF indicative of the thermoelectric characteristics of the test piece. As can be readily be appreciated, minor changes in the temperature of the heated probe can cause substantial errors or drift in the net EMF developed, thereby causing an improper test result.

Similarly, such prior art devices are subject to error due to changes in the temperature differential between the heated and cooled electrodes. That problem has been addressed in the above noted Tevotest 3.205. In the Tevotest 3.205 both electrodes are heated to establish a constant temperature therebetween. The temperatures of the probes are continuously monitored through thermocouples.

SHORT STATEMENT OF THE INVENTION

The present invention provides an apparatus with sufficient resolution to distinguish between test pieces of the same alloy but having different relative proportions in their composition. Further sensitivity to drift in the probe temperature, temperature differential of the two probes, ambient temperature or test piece temperature is substantially eliminated. This is accomplished by utilizing two thermoelectric probes placed in contact with the test piece, with one probe heated to a predetermined temperature greater than the temperature of the other probe. The probes comprise electrodes of a thermally conductive material having in thermoelectric circuits, each having differing predetermined thermoelectric characteristics. A variable voltage divider (null balance potentiometer) electrically couples the respective thermoelectric circuits of the probe. The output terminals of the null balance voltage divider networks are connected in series opposition through an indicator and are mechanically or electronically slaved to assure that they are adjusted in synchronism. An indicator cooperating with the voltage divider adjustment mechanism provides an indication of the relative adjustment position of the voltage dividers. The adjustment position of the voltage dividers which produces a null as between the output signals from the respective probes is indicative of the thermoelectric characteristics of the test piece relative the material of the electrode. Such probe circuitry effectively desensitizes the apparatus to changes in test probe termperature, temperature differential of the two probes, ambient temperature, and the temperature of the test piece. The temperature desensitization serves to extend the resolution of the apparatus to, for example, 1.0 millimeter of meter movement per approximately 0.25 microvolts. The maximum sensitivity provided by the Tevotest is 1.0 millimeter of meter movement per 20 microvolts.

The thermoelectric circuits of the probes are suitably comprised of a conductor of a thermoelectric material (thermocouple) in thermal contact with the electrode and coupled back to the electrode through a zeroing adjustment potentiometer or variable voltage divider network to form a thermoelectric circuit.

In accordance with another aspect of the invention, simple calibration means are provided. Thermocouples of material that produce thermoelectric potentials are equal to or less than the thermoelectric potential of those materials used in the thermoelectric circuits. The thermoelectric circuits are thermally coupled to the respective electrodes and electrical connection between corresponding calibration on the respective probe electrodes is effected. The null balance voltage dividers are then adjusted manually or automatically to a desired setting and the zero adjustment voltage divider of the corresponding thermoelectric circuits are adjusted until a null indication is generated to thereby calibrate or recalibrate the test range. Thus, the need to use test pieces for periodically rechecking the range calibration as in the prior art, is eliminated. This is advantageous in that possible error by different test operators and the possibility of losing or misplacing the range calibration specimens are eliminated.

In accordance with a further aspect of the present invention, provisions are made for establishing further discriminants between alloy compositions by using diverse probe contact materials, generating a magnetic field across the probe/test piece junction to vary the thermoelectric characteristics thereof, varying the temperature of electrode contacts, generating bias voltage across the probe/test piece junctions, and comparison of the voltage/ampere ratios of alloys.

BRIEF DESCRIPTION OF THE DRAWINGS

A preferred exemplary embodiment will hereinafter be described in conjunction with the appended drawings wherein like numerals refer to the elements and.

DETAILED DESCRIPTION OF THE PREFERRED EMBODIMENT

Figure 1:
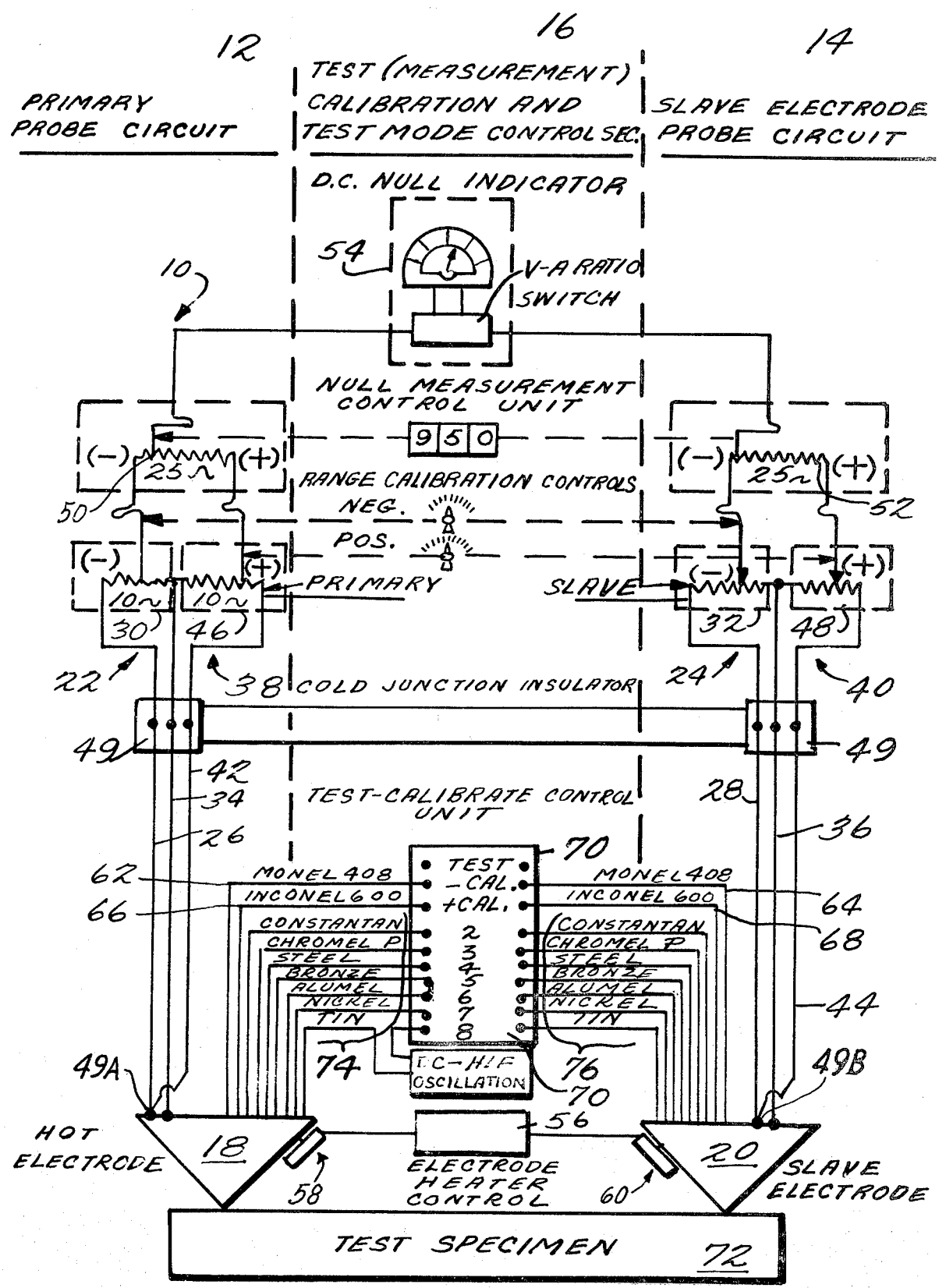
FIG. 1 is a schematic drawing of a thermoelectric analyzer in accordance with the present invention.

Referring now to FIG. 1, a thermoelectric analyzer, in accordance with the present invention, generally indicated as 10, comprises a primary probe circuit 12, a slave probe circuit 14, and a test measurement calibration and test probe control section 16. Probes 12 and 14, respectively, include electrodes 18 and 20 formed of a material having high thermal conductivity such that the temperature is constant throughout. Suitable materials are copper, gold or silver. As is well known, it is desirable that the electrodes be relatively massive and include a small contact tip to effect good electrical contact with the test specimen but providing only minimal thermal transfer between the probe and test piece.

Thermoelectrically connected to electrodes 18 and 20, are first thermoelectric circuits 22 and 24, respectively, having substantially identical predetermined thermoelectric characteristics.

Thermoelectric circuits 22 and 24 each include a conductor, 26 and 28 respectively, of a first thermoelectric material such as Constantan. Conductors 26 and 28 are each electrically coupled at one end to a thermoelectric conductor, 42 and 44, respectively. The coupling of conductor 26 to conductor 42 occurs at a junction 49A and the coupling of conductor 28 to conductor 44 occurs at a junction 49B. Conductors 26 and 42, at junction 49A, are thermoelectrically coupled to electrode 18. Conductors 28 and 44, at junction 49B, are thermally or thermoelectrically coupled to electrode 20. Conductors 26 and 28 are respectively electrically coupled to adjustable voltage dividers 30 and 32 through cold junction insulators 49. Dividers 30 and 32 are for zeroing and range adjustment and their operation will be more fully set forth below.

The thermoelectric circuits are respectively completed by further conductors 34 and 36 suitably formed of the same material as the electrodes electrically connecting adjustable divider networks 30 and 32 respectively to electrodes 18 and 20.

Also thermoelectrically connected to electrodes 18 and 20 are respective second thermoelectric circuits 38 and 40. Second thermoelectric circuits 38 and 40 are chosen to have substantially identical predetermined thermoelectric characteristics differing from the thermoelectric characteristics of the first thermoelectric circuits 22 and 24. Second thermoelectric circuits 38 and 40 are suitably formed of conductors 42 and 44, respectively, both formed of a thermoelectric material different from that forming first conductors 26 and 28, suitably Chromel P. Conductors 42 and 44 are suitably thermoelectrically or thermally connected to thermoelectric conductors 26 and 28 at junctions 49A and 49B and thermally or thermoelectrically coupled to their associated electrodes (18, 20). Conductors 42 and 44 are electrically connected at their other end through cold junction insulator 49 to one input terminal of respective variable voltage divider networks 46 and 48. Variable voltage divider networks 46 and 48 are similar to divider networks 30 and 32 and are utilized for zeroing and range adjustment. The electrical circuit is completed by electrically connecting divider networks 46 and 48 to the probe electrodes 18 and 20 through conductors 34 and 36, respectively.

As noted above, the connection between thermocouple conductors 26, 42, 28 and 44 and conductors 34 and 36 to associated calibration voltage divider networks 30, 46, 32 and 48 are effected, in conventional cold junction insulator 49. Cold junction insulator 49 prevents any spurious thermoelectric interactions at the juncture between the respective conductors. Further, insulator 49 may be maintained, if desired, at a constant temperature below room temperature, by a thermoelectric cooling module.

The thermoelectric characteristics of first thermoelectric circuits 22 and 24 and second thermoelectric circuits 38 and 40 are suitably chosen to produce EMF's of opposite polarity, to provide thereby a wide range of measurement, as will be explained. It should be appreciated that any thermoelectric circuit having known thermoelectric characteristics can be utilized. For example, thermopile circuits can be utilized to provide an extended range of measurements.

Adjustable voltage divider networks 30, 32 and 46, 48 provide for trimming and calibrating the measurement range. The calibration (zero adjust) divider networks (30, 32) of thermoelectric circuits 22 and 24 and the calibration potentiometers 46 and 48 of second thermoelectric circuits 38 and 40 are respectively slaved together to provide for synchronous adjustments of the respective first circuits and respective second circuits.

The output EMF's of thermoelectric circuits 22 and 38, and 24 and 40 are respectively applied to variable voltage divider networks 50 and 52 (hereinafter referred to as null balance potentiometers 50 and 52). Null balance potentiometers 50 and 52 are also mechanically or electronically slaved for adjustment in synchronism. The adjustment mechanism also suitably includes an indicator providing indicia of the relative adjustment position of the null balance potentiometers. The output terminals of null balance potentiometers 50 and 52 are connected in series opposition through a suitable indicator device such as a DC null indicator, ammeter, voltmeter. Provisions for recording the measurements, such as by a strip chart can also be included. In the preferred embodiment, a voltmeter/ammeter 54 is utilized. A "go/no-go" test lamp may also be included, if desired to indicate whether the test is valid or to detect mixed alloys.

The respective temperatures of electrodes 18 and 20 are controlled by a conventional heating unit such as a resistance heating system generally indicated as 56. If desired, the temperature of each electrode can be continually monitored through thermocouples 58 and 60 to maintain a constant temperature difference between electrodes. The temperature of the electrodes are suitable 150° F. for electrode 18 and 100° F. for electrode 20. It is noted that while maintaining such contant temperature differences through thermocouples is desirable, it is somewhat redundant in that small drifts in temperature difference are compensated for by the probe circuitry as will be explained.

Variable voltage dividers 30, 32, 46 and 48 are suitably, as shown in FIG. 1, simple potentiometers. However, finer calibration adjustment and tester resolution can be achieved by utilizing a variable divider with multiple adjustments. Such voltage dividers are shown in FIG. 2.

Figure 2:
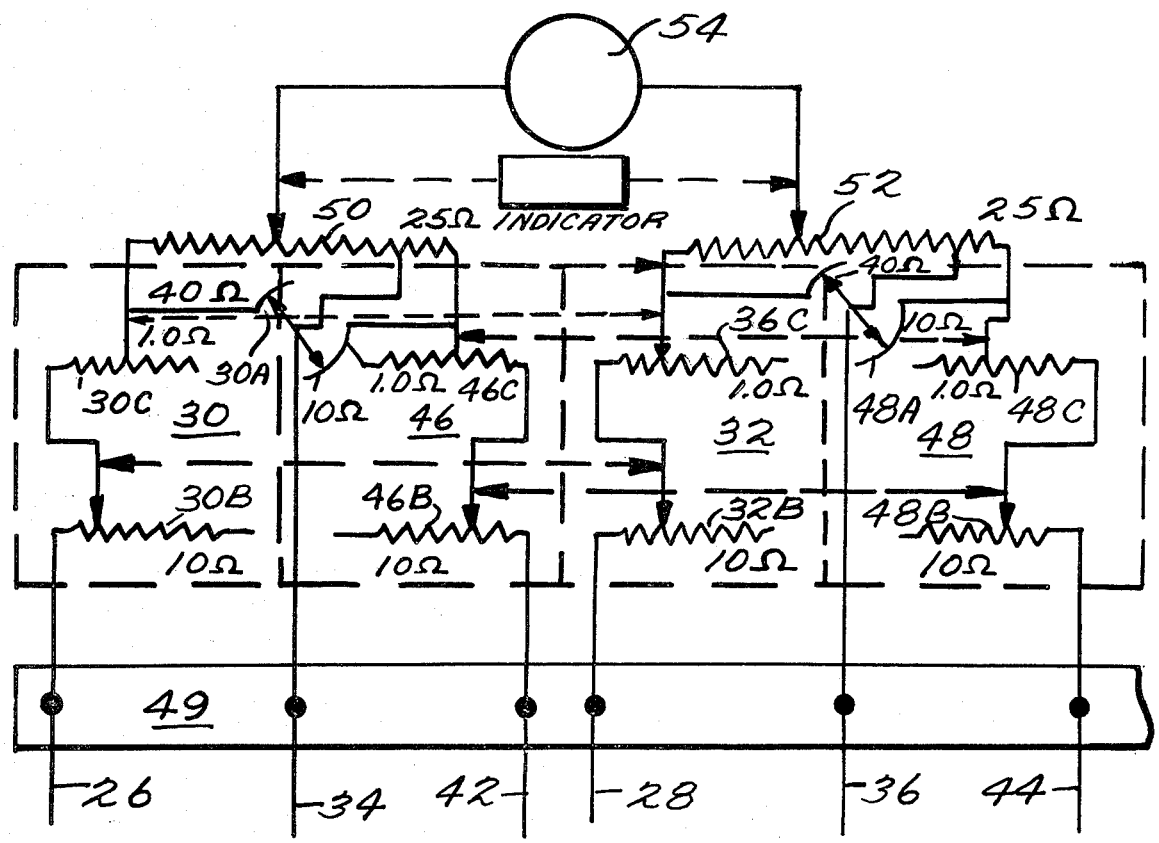
FIG. 2 is an alternative embodiment of the variable voltage divider circuits of FIG. 1.

Referring now to FIG. 2, variable voltage dividers 30, 32, 46 and 48 respectively comprise plural potentiometers 30A, 30B, 30C; 32A, 32B, 32C; 46A, 46B, 46; and 48A, 48B, 48C. Corresponding potentiometers in dividers 30 and 32 and corresponding potentiometers in dividers 46 and 48 are mechanically slaved. In addition, potentiometers 30A and 46A, and 32A and 48A are also slaved together. Potentiometers 30A and 46A together comprise an amperage adjustment mechanism for probe 12. Conductors 34 and 36 can be, if desired, electrically connected to predetermined points taps in null balance potentiometers 50 and 52, corresponding to the "null point" of the material of the electrode to reduce the resistance of the circuit. Potentiometers 30B, 32B, 46B and 48B provide for course range adjustment while potentiometers 30C, 32C, 46C and 48C provide for fine zero adjustment.

Referring again to FIG. 1, calibration and test mode control section 16 also includes provisions for ready calibration. Respective conductors 62 and 64 both formed of a material, suitably Monel alloy 408, generating a thermoelectric potential in cooperation with the electrodes when first conductors 26 and 28 are thermoelectrically connected to electrodes 18 and 20. Similarly, conductors 66 and 68 formed of a material which generates a thermoelectric potential in cooperation with the electrodes suitably Inconel Alloy 600 and the second conductors 42 and 44 are also thermoelectrically coupled to electrodes 18 and 20, respectively.

A switch 70, suitably a ten position selector switch, selectively effects electrical connection between conductors 62 and 74 to provide for calibration of first thermoelectric circuits 22 and 24. That is, the electrical connection is completed by switch 70, and calibration dividers 30 and 32 are adjusted until a predetermined indication is achieved on indicator 54 (a null indication) at the lowest adjustment of null balance potentiometers 50 and 52). Electrical connection is then effected between conductors 66 and 68 and calibration dividers 46 and 48 adjusted to provide a null indication at the highest desired reading of adjustment for null balance potentiometers 50 and 52. Switch 70 provides an open circuit during the actual test mode operation. As will hereinafter be discussed, switch 70 also provides for selectively effecting electrical connections between other thermoelectric conductors coupled to electrodes 18 and 20 to provide for a biasing discriminant.

In operation, electrodes 18 and 20 are brought into thermoelectric contact with a test specimen 72. The electrodes are relatively disposed on the test specimen (e.g., within two inches of each other) so that there is no appreciable difference in the two points of contact. The respective first and second thermoelectric circuits then produce respective EMF's indicative of an algebraic sum of the EMF produced by the thermoelectric EMF produced by the interaction of the circuit with the electrodes. As noted above, test result variables due to changes in temperature of electrode 20 are compensated for by slaving the respective voltage dividers of primary probe circuit 14 to the corresponding voltage dividers associated with slave probe circuit 12. The thermoelectric circuits generate a voltage drop across the respective calibration potentiometers. Null balance potentiometer 50 is then adjusted until a null indication is provided on indicator 54. The numerical readout indicative of the adjustment position of the null balance potentiometers is indicative of the relationship of the termoelectric EMF output of the test specimen relative that of the thermoelectric circuits. The ratio of thermoelectric EMF's is constant irrespective of any change in voltage drop across either or both potentiometers. Each piece of a production lot having the same chemical composition and production history (hot or cold working) should generate a substantially identical test result. Thus, the null balance adjustment indication is representative of the termoelectric characteristics of the test piece 72 relative the known thermoelectric characteristics of the probes, and thus provides an indication of the alloy-composition. Thus, analyzer 10 can be used by metal production inspectors to confirm the identity of known alloys or to establish the identity of unknown alloys, and more importantly, to rapidly detect and sort any inferior alloys which inadvertently may become mixed during one of many production process stages. This test is non-destructive, rapid, reliable, economical, simple to use, easy to calibrate and gives the same test result for all test operators.

The apparatus is used to measure the null balance of the thermoelectric output of each metal or alloy. The test result is expressed as a numerical value within an empirically predetermined range of values from 000 to 999.

For example, using Chromel P and Constantan thermocouples in thermoelectric circuits 38 and 40 and 22 and 24 respectively, with relative adjustment scale ranging from 050 (Inconel 600) to 950 (Monel 408), means deviation readings are manifested as is set out in Table 1:

TABLE I

RELATIVE THERMOELECTRIC POTENTIALS FOR METALS AND NICKEL BASE ALLOYS

Null balance adjustment indication with EMF measured in millivolts for copper probe and null shift with chemistry using other probes

| Metal, alloy or alloy code | Copper (Basic test) | | Iron | Nickel | Phosphoros Bronze |
|---|---|---|---|---|---|
| | Null Point | Actual Millivolts output | | | |
| Chromel P | | * | | | (+.346) |
| | 709 | * | | | (+.283) |
| | 603 | 033 | | | (+.162) |
| Inconel Alloy | 600 | 050 | | | (+.143) |
| | 700 | 065 | | | |
| Titanium | | 078 | | | (+.114) |
| | 604 | 092 | | | (+.100) |
| | 702 | 095 | | | |
| | 751 | 105 | | | |
| Chromium | | 110 | | | (+.077) |
| | 750 | 115 | | | |
| | 606 | 120 | | | |
| Molybdenum | | 144 | | | (+.048) |
| Iron | | 171 | | | (+.021) |
| Tungsten | | 181 | | | (+.011) |
| Copper | | 192 | | | (+.002) |
| | 625 | 195 | | | |
| | 718 | 210 | | | |
| | 901 | 215 | | | |

TABLE I-continued

RELATIVE THERMOELECTRIC POTENTIALS FOR METALS AND NICKEL BASE ALLOYS

Null balance adjustment indication with EMF measured in millivolts for copper probe and null shift with chemistry using other probes

| Metal, alloy or alloy code | Copper (Basic test) | | Iron | Nickel | Phosphoros Bronze |
|---|---|---|---|---|---|
| | Null Point | Actual Millivolts output | | | |
| | 803 | 229 | (−.037) | | | |
| Aluminum | | 238 | (−.046) | | | |
| | 825 | 240 | | | | |
| | 804 | 245 | | | | |
| Magnesium | | 246 | (−.054) | | | |
| Lead | | 250 | (−.058) | | | |
| Tin | | 250 | (−.058) | | | |
| | 800 | 250 | (−.058) | | | |
| | 801 | 255 | | | | |
| | 805 | 260 | | | | |
| | 902 | 270 | | | | |
| Nickel (4% Ti) | 209 | 320 | (−.108) | 367 | 410 | 430 |
| Nickel (3% Ti) | 208 | 384 | (−.192) | 400 | 483 | 450 |
| | 300 | 495 | | | | |
| Nickel (99%) | 200 | 520 | | 410 (−) | 627 (+) | 480(−) |
| Cobalt | | 526 | (−.334) | | | |
| Nickel (4% Al) | 301 | 542 | (−.350) | 582 | 595 | 642(+) |
| Alumel | | 558 | | | | |
| | 418 | 570 | | | | |
| | 409 | 595 | | | | |
| | 212 | 610 | | | | |
| | 211 | 725 | | | | |
| | 501 | 760 | | | | |
| | K500 | 765 | | | | |
| Monel (Ni—Cu) | 400 | 800 | | | | |
| | R405 | 810 | | | | |
| | 406 | 825 | | | | |
| | 412 | 845 | | | | |
| | 413 | 855 | (−.718) | | | |
| | 416 | 855 | | | | |
| | 407 | 860 | | | | |
| | 402 | 905 | | | | |
| Monel Alloy | 408 | 950 | (−.806) | | | |
| | 403 | 975 | | | | |
| | 258 | 985 | | | | |
| Constantan | | * | (−.941) | | | |

*Off scale, beyond null range

It is noted, however, that particular null balance indication results are not always unique to a particular alloy; in some instances, the range of test results for one alloy overlaps the range of tests for other alloys of similar chemistry. Accordingly, further discriminants must be utilized to distinguish between alloys having substantially identical null balance indications. Accordingly, means are provided in analyzer control section 16 for providing a bias voltage/current between the respective electrodes and the test specimen. The present inventor has discovered that the thermoelectric EMF versus bias voltage characteristics of various alloys are different and accordingly, EMF null balance measurements under different biasing conditions can be utilized as a discriminant between such alloys. Accordingly, a thermoelectric bias is provided by selectively effecting electrical connections between thermocouples thermoelectrically connected to the respective electrodes. Such thermocouples are generally indicated in the drawing by the numerals 74 and 76. Selective electrical connection is established by switch 70. In operation, to perform the bias tests, switch 70 is switched from its open circuit normal test mode condition to establish electrical connections between thermocouples 74 and 76. Any deviation from a null indication in response to the establishing of a particular bias circuit is noted and compared to predetermined characteristics of various test specimens to distinguish between alloy compositions. It should be appreciated that such biasing may be accomplished by any variable DC source. Additionally, further discriminating information can be provided by utilizing probe tips of diverse materials. For example, alloys containing nickel of small amounts of titanium or aluminum show, as can be seen from TABLE I, a marked deviation in null point when a measurement is taken with an iron, nickel or phosphorus bronze contact tip opposed to copper. Other contact tip materials may, of course, be found more effective for distinguishing between other metals or alloys. A probe structure facilitating such measurements is shown in FIG. 3.

Figure 3:
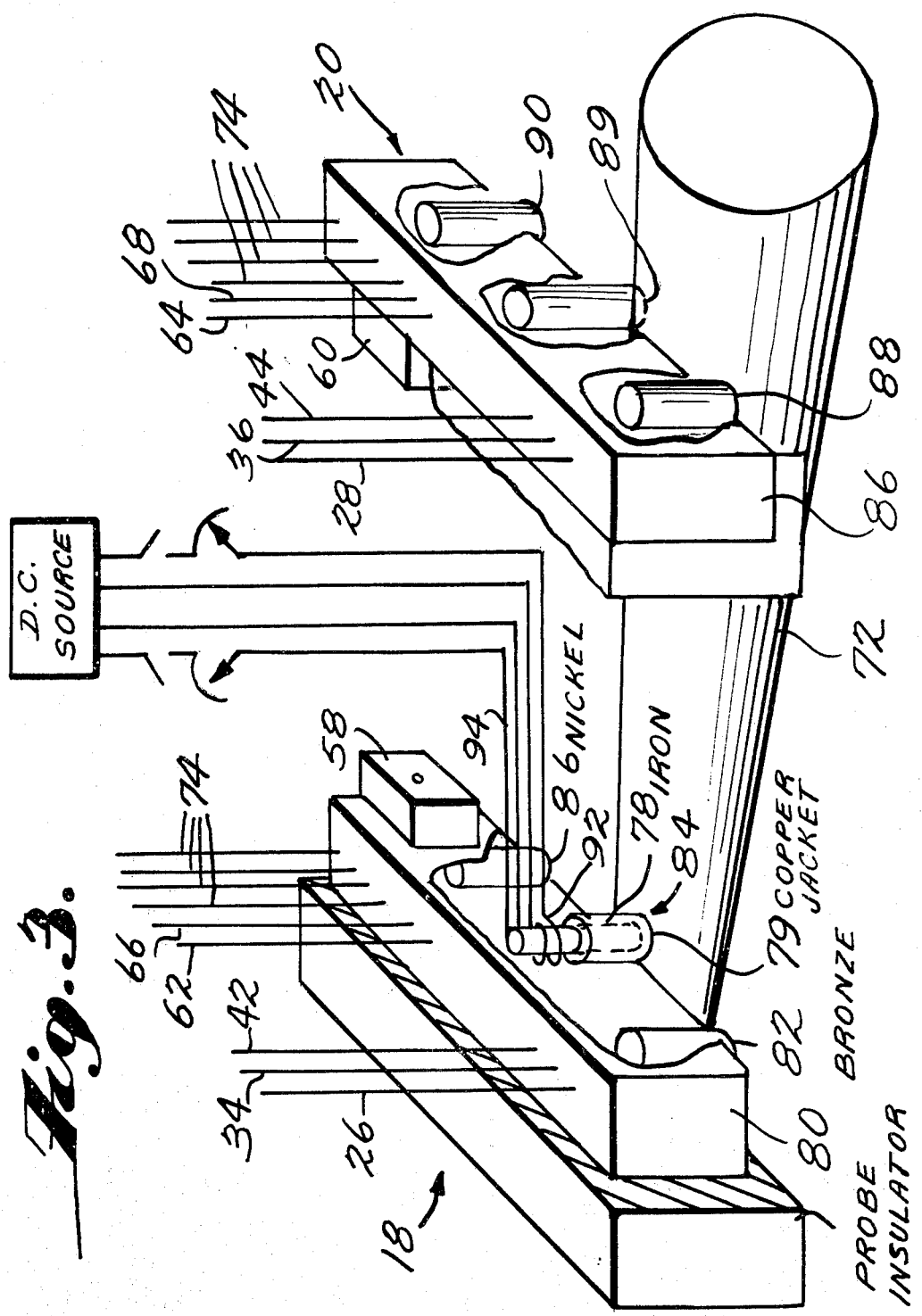
FIG. 3 is a pictorial schematic of electrodes 18 and 20 in accordance with the present invention.

Referring now to FIG. 3, electrode 18 comprises a copper block 80 having journaled therein probe tips 82, 84 and 86. Tips 82, 84 and 86 are formed of bronze and nickel respectively. Probe tip 84 is formed of a copper jacket 79 over an iron core 78 (electrically insulated therefrom). Each probe tip 84 is in thermal equilibrium with block 80 (including the copper jacket 79). Similarly, electrode 20 comprises a copper block 86 having journaled therein respective probe tips 88, 89 and 90, all suitably formed of copper. Tips 88, 89 and 90 are relatively disposed at different distances along the central axis of the bottom of block 86, to facilitate measurement of test piece rods of varying diameter. In operation, electrode 18 is tilted to bring the desired probe tip or tips into contact with the test piece.

A further discriminant is provided by establishing a magnetic field across the thermoelectric junction of primary electrode 18 and test specimen 72. This is accomplished by the inclusion of copper jacketed iron core probe tips within electrode 18. A coil 92 of insulated wire cooperating with an adjustable DC power supply is wound about iron core 78. It has been found that superimposing a magnet field over the thermoelectric junction alters the null balance adjustment point (indication) of various alloys. It has been found that this effect is manifested in non-magnetic as well as magnetic alloys, and that the magnetic field strength-thermoelectric EMF characteristic can be utilized to distinguish between various of such alloys.

Further, it has been found that an additional discriminant can be provided by varying the temperature of electrode probe tip 84. For example, while the normal test temperature of electrode 18 is typically 150° F., the null balance adjustment position for the elemental metal iron will shift on the relative thermoelectric scale notably in response to a change of 20° or more. Alloys containing iron similarly shift in null balance adjustment position but to a lesser degree depending upon the amount of iron in the composition and the presence or absence of various counteracting elements.

The temperature of electrode 18 can be varied by altering the power supplied to the electrode heater. Further, changes in temperature can be effected in probe tip 84 through the Peltier effect by altering the direction of current applied to core 78 through conductors 94 (connected to each end of core 78).

Figure 4:
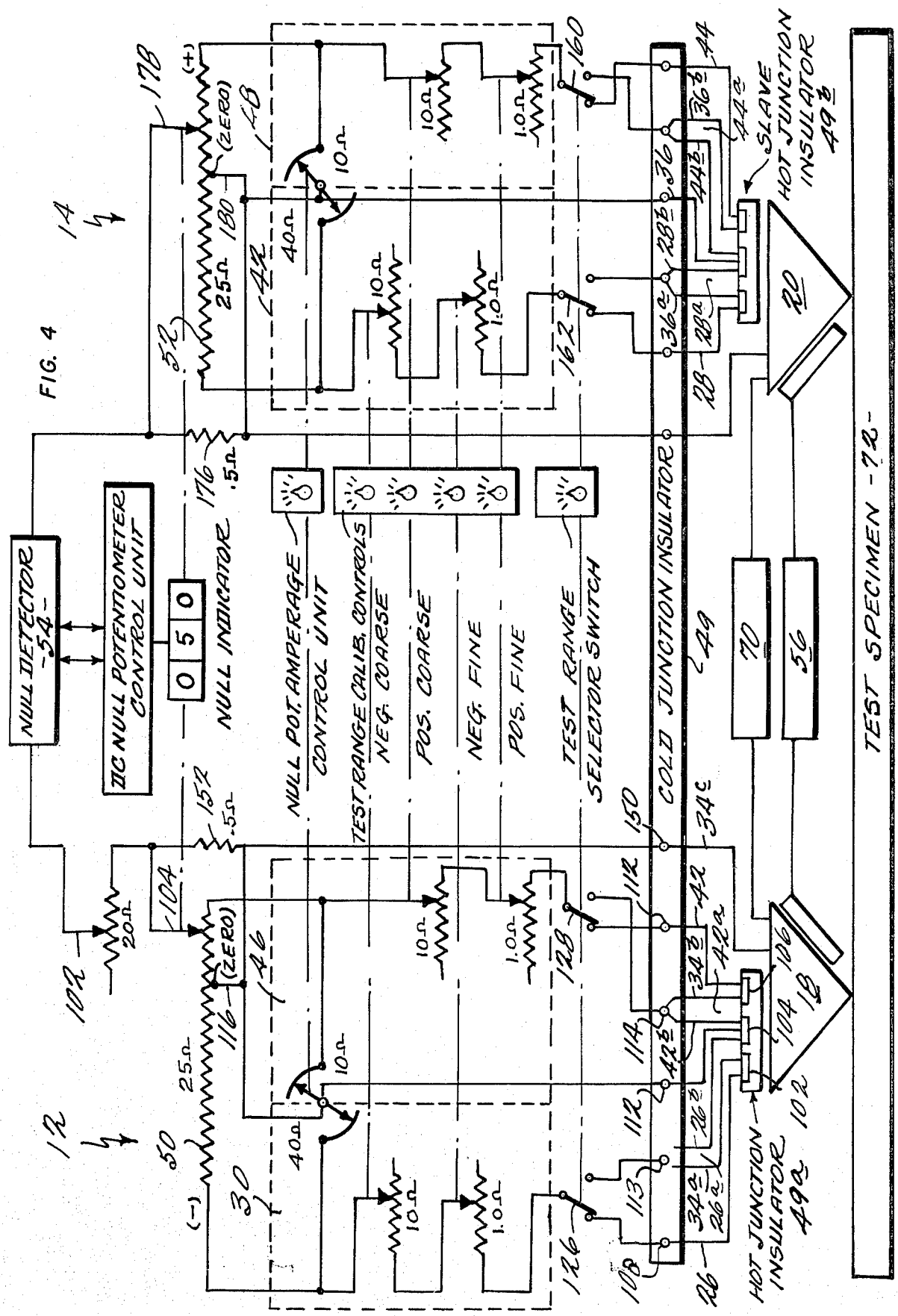
FIG. 4 is a schematic diagram of an alternate embodiment of the thermoelectric analyzer in accordance with the present invention.

Referring now to FIG. 4, there is shown an alternate embodiment of the thermoelectric analyzer in accordance with the present invention. Reference numerals used in FIG. 4 that are identical with those numerals used in the preceding figures refer to identical or corresponding parts to those shown on the preceding drawings. The same reference numeral applied to multiple conductors indicates that the identical material is used for those conductors.

In the embodiment of FIG. 4, provisions are made for controllably expanding the test range of the apparatus by selectively changing the first and second thermoelectric circuits in the system. Electrically or mechanically slaved switches 126, 128, 162 and 160 alternatively couple (through cold junction insulator (CJI) 49 either conductors 26 and 42 and conductors 28 and 44 or thermopiles 26a and 42a and thermopiles 28a and 44a to range calibration circuitry analogous to that shown in FIG. 2.

Thermopiles 26a, 42a, 28a and 44a are suitably formed of joined conductors made of the same materials as conductors 26 and 34, 42 and 34, 28 and 36, and 44 and 36. More particularly, the various conductors 26, 34, and 42, are thermally coupled to, but electrically insulated from electrode 18, by a hot junction insulator (HJI) 49A. Similarly, the various conductors 28, 36, and 42 are thermally connected to but electrically insulated from electrode 20 by a hot junction insulator (HJI) 49B. Conductors 26, 34 and 42 between a first (102), second (104) and third (106) junction in HJI 49A, and first (108), second (110) and third (112) junctions in CJI 49. A second conductor 34a of the same material as electrode 18 is electrically connected to conductor 26 at HJI junction 102 and is connected to a fourth CJI junction 113. A second conductor 26b suitably of the same material as conductor 26 is also connected between CJI junction 113 and HJI junction 104 to form thermopile 26a. At HJI junction 104, conductor 26a is electrically connected to conductor 34, and to a conductor 42b suitably of the same material as conductor 42. Conductor 42b is connected to a fifth junction 114 in CJI 49, whereat it is electrically connected to a conductor 34b, of the same material as electrode 18 to form thermopile 42a. Conductor 34b is also electrically connected to conductor 42 at HJI junction 106. Conductor 28, 36 and 44 are similarly connected between junctions in HJI 49B and CJI 49 and thermopiles 28a and 44a are similarly formed by conductors 36a, 28b, 44b and 36b also coupled between junctions in HJI 49B and CJI 49.

Further, in the embodiment of FIG. 4, the thermoelectric current generated by the probe/test piece contact, in effect bypasses the resistances associated with range calibration. The embodiment of FIG. 4 thus provides more sensitivity to thermoelectric potentiometers of lesser magnitudes than does the embodiment of FIG. 1. Conductors 34 and 36 (of the same material as electrodes 18 and 20, respectively) are electrically connected to electrodes 18 and 20, and are coupled through cold junction insulator 49 to small resistors (e.g. 0.5) 152 and 176. Resistor 152 is connected, through a variable resistance 102 to one input of null detector 54. Resistor 102 compensates for the low resistance of the branch of the circuit electrically connected to the electrode, and controls the biasing EMF to null indicator 54. Resistor 176 is coupled to the other input of null detector 54. Conductors 34 and 34c and 36 and 36c are coupled to taps 116 and 180 in potentiometers 50 and 52, corresponding to the null points of the materials of electrodes 18 and 20. Thus, the thermoelectric potential relationship of alloys to the standards (here Constantan and Chromel P) is not altered from those applicable to FIG. 1. The wipers 104 and 178 of applicable to FIG. 1. The wipers 104 and 178 of potentiometers 50 and 52 are connected to resistors 152 and 176, on the opposite sides thereof from the connection to taps 116 and 180.

As in the embodiment of FIG. 1, analysis of the test piece 72 is effected by placing electrodes 18 and 20 into thermoelectric contact with test piece 72. A thermoelectric EMF is then generated by the contact points, providing a current through resistors 156 and 176. Concurrently, thermoelectric EMFs of opposite polarity are generated by the first and second thermoelectric circuits thermally connected to the electrode. Slaved potentiometers 50 and 52 are then adjusted until the respective EMFs cancel (i.e. provide a null). The adjustments to the potentiometers 50 and 52 provide indica of the composition of test piece 72, as previously explained.

Utilizing the apparatus described, an operator can control the voltage at or current through test piece junctions. It is possible to vary the current during testing as an aid to sorting test pieces of similar alloys.

It will be understood that the above description is of an illustrative embodiment of the present invention and that the invention is not limited to the specific form shown. For example, it should be appreciated that the metal alloy analyzer 10 in accordance with the present invention can readily be adapted to cooperate with a computer such that each of the tests is performed in sequence until a result is obtained which uniquely identifies the composition of the rest piece. Also, variable resistances can be used for resistors 152 and 176. Modifications may be made in the design and arrangement of the elements without departing from the spirit of the invention as expressed in the following claims:

What is claimed is:

1. Apparatus for providing indicia of the metal alloy composition of a test piece comprising:

first and second thermoelectric probes adapted for thermoelectrically contacting said test piece, each probe including an electrode, first and second thermoelectric circuits thermally coupled and electrically connected to said electrode, and a variable voltage divider electrically coupling said first and second thermoelectric circuits, said first and second thermoelectric circuits having different predetermined thermoelectric characteristics;

said apparatus further comprising means for adjusting the variable voltage divider of said first and second probes together in synchronism; and means for electrically coupling said variable voltage dividers in series opposition and for providing indicia of the relative adjustment of said variable voltage dividers.

2. Apparatus for testing the metal alloy composition of a test piece, said apparatus being of the type including first and second thermoelectric probes for contacting said test piece and generating signals indicative of their respective thermoelectric interaction therewith, means for maintaining one of said probes at a predetermined temperature greater than the temperature of the other, and indicator means coupled to said first and second probes for providing indicia of the relative amplitude of said signals, wherein:

said first and second probes each include an electrode of a first thermally conductive material, a first conductor of a second material and a second conductor of a third material, respectively coupled to said electrode and forming first and second thermoelectric junctions therewith, said first and second thermojunctions generating first and second thermoelectric potentials, respectively; and a third conductor of said first material coupled to said electrode; first, second and third voltage variable divider means, for generating, at an output terminal thereof, a signal indicative of a controlled fraction of the potential difference between first and second input terminals thereof, said first voltage divider means first and second input terminals being connected to said first conductor and said third conductor respectively and said second voltage divider means first and second input terminals being connected to said second conductor and third conductor respectively; said third voltage divider means first and second input terminals being connected to said first voltage divider means output terminal and said second voltage divider means output terminal, respectively; and said first and second probe third voltage divider output terminals being coupled to said indicator means, electrically coupling said probes in series opposition;

said apparatus further comprising means for adjusting said first and second probe first voltage divider means in synchronism;

means for adjusting said first and second probe second voltage divider means in synchronism; and means for adjusting said first and second probe third voltage divider means in synchronism.

3. The apparatus of claims 1 or 2 further comprising biasing means, coupled between said first probe electrode and said second probe electrode, for selectively providing a potential difference therebetween.

4. The apparatus of claim 2 wherein said apparatus further comprises respective fourth conductors formed of a predetermined thermoelectric material, respectively, thermoelectrically connected to said first probe electrode and said second probe electrode and means for selectively effecting an electrical connection between said respective fourth conductors for generating a thermoelectric bias between said probes.

5. The apparatus of claims 1 or 2 wherein said apparatus further comprises respective sets of conductors formed of predetermined thermoelectric material thermoelectrically connected to said first probe electrode and to said second probe electrode, respectively; and means for selectively effecting electrical connections between corresponding conductors in said sets to selectively generate a thermoelectric bias between said probes.

6. The apparatus of claims 1 or 2 further including means for calibrating said apparatus.

7. The apparatus of claim 2 futher including means for calibrating said apparatus, said calibration means comprising:

respective fourth conductors formed of said second material respectively coupled to said first probe electrode and said second probe electrode;

respective fifth conductors formed of said third material and respectively thermoelectrically connected to said firts probe electrode and said second probe electrode; and means for selectively effecting electrical connections between said respective fourth conductors and selectively effecting electrical connections between said respective fifth conductors.

8. The apparatus of claims 1 or 2 wherein said first probe further includes means for generating a magnetic field in the area of contact between said first probe electrode and said test piece.

9. The apparatus of claim 8 wherein said means for generating a magnetic field comprises an iron core electrically insulated from a copper jacket disposed in said first contact means electrode said iron core having a coil of insulated wire disposed thereabout and means for controllably applying a signal to said coil.

10. The apparatus of claim 1 wherein said means for adjusting said variable voltage divider includes means for providing indicia of the amount of said adjustment.

11. The apparatus of claims 1 or 2 wherein said first probe electrode further includes:

a core of a ferrous material;

an insulated conductor connected at each end of said core; and means for selectively applying DC current to said core to controllably vary the temperature of the contact point between said first probe electrode and said test piece, in accordance with a Peltier effect.

12. Apparatus for testing the metal alloy composition of a test piece, said apparatus being of the type including first and second thermoelectric probes for contacting said test piece and generating signals indicative of their respective thermoelectric interaction therewith, means for maintaining one of said probes at a predetermined temperature greater than the temperature of the other, and indicator means coupled to said first and second probes for providing indicia of the relative amplitude of said signals, wherein:

said first and second probes each include an electrode of a first thermally conductive material, a first conductor of a second material, a second conductor of a third material and a third conductor of said first material, said first and second and third conductors being electrically coupled to one another at junctions thermally coupled to said electrode to form first and second thermoelectric junctions, said first and second thermojunctions generating first and second thermoelectric potentials respectively; and a fourth conductor of said first material electrically coupled to said electrode;

first, second and third voltage variable divider means, for generating, at an output terminal thereof, a signal indicative of a controlled fraction of the potential difference between first and second input terminals thereof;

said first voltage divider means first and second input terminals being connected to said first conductor and said third conductor respectively said second voltage divider means first and second input terminals being connected to said second conductor and third conductor respectively;

said third voltage divider means first and second input terminals being connected to said first voltage divider means output terminal and said second voltage divider means output terminal, respectively;

a resistance;

said fourth conductor being coupled through said resistance to said indicator means;

said first and second probe third voltage divider output terminals also being coupled to said indicator means, electrically coupling said probes in series opposition;

said apparatus further comprising means for adjusting said first and second probe first voltage divider means in synchronism;

means for adjusting said first and second probe second voltage divider means in synchronism; and means for adjusting said first and second probe third voltage divider means in synchronism.

13. The apparatus of claim 12 further comprising biasing means, coupled between said first probe electrode and said second probe electrode, for selectively providing a potential difference therebetween.

14. The apparatus of claim 12 wherein said apparatus further comprises respective fourth conductors formed of a predetermined thermoelectric material, respectively, thermoelectrically connected to said first probe electrode and said second probe electrode and means for selectively effecting an electrical connection between said respective fourth conductors for generating a thermoelectric bias between said probes.

15. The apparatus of claim 12 wherein said apparatus further comprises respective sets of conductors formed of predetermined thermoelectric material thermoelectrically connected to said first probe electrode and to said second probe electrode, respectively; and means for selectively effecting electrical connections between corresponding conductors in said sets to selectively generate a thermoelectric bias between said probes.

16. The apparatus of claim 12 further including means for calibrating said apparatus.

17. The apparatus of claim 12 further including means for calibrating said apparatus, said calibration means comprising:
respective sixth conductors formed of said second material respectively coupled to said first probe electrode and said second probe electrode;
respective fifth conductors formed of said third material and respectively thermoelectrically connected to said first probe electrode and said second probe electrode; and
means for selectively effecting electrical connections between said respective fifth conductors and selectively effecting electrical connections between said respective sixth conductors.

18. The apparatus of claim 12 wherein said first probe further includes means for generating a magnetic field in the area of contact between said first probe electrode and said test piece.

19. The apparatus of claim 12 wherein said means for generating a magnetic field comprises an iron core electrically insulated from a copper jacket disposed in said first contact means electrode said iron core having a coil of insulated wire disposed thereabout and means for controllably applying a signal to said coil.

20. The apparatus of claim 12 wherein said means for adjusting said variable voltage divider means includes means for providing indicia of the amount of said adjustment.

21. The apparatus of claim 12 wherein said probe electrode further includes:
a core of a ferrous material;
an insulated conductor connected at each end of said core; and
means for selectively applying DC current to said core to controllably vary the temperature of the contact point between said first probe electrode and said test piece, in accordance with a Peltier effect.

22. The apparatus of claim 12 further including a hot junction insulator for coupling said first, second and third conductors to said electrode.

23. The apparatus of claim 1, further including means for selectively changing the respective predetermined characteristics of said first and second thermoelectric circuits.

24. The apparatus of claim 1 wherein each probe includes a plurality of thermoelectric circuits each having different predetermined thermoelectric characteristics thermally connected to said electrode; and
said apparatus further comprising means for switchably effecting in synchronism electrical connection between corresponding selected ones of said plurality of thermoelectric circuits and the variable voltage dividers of said first and second probes.

25. The apparatus of claim 12 wherein said each of said probes further include at least one alternate thermoelectric circuit, thermally connected to said electrode; and
said apparatus further comprises means for selectively effecting, in synchronism on both said probes, electrical connection between first voltage divider and said first and third conductors to or between said first voltage divider and said alternate thermoelectric circuit.

26. Apparatus for testing the metal alloy composition of a test piece, said apparatus being of the type including first and second thermoelectric probes for contacting said test piece and generating signals indicative of their respective thermoelectric interaction therewith, means for maintaining one of said probes at a predetermined temperature greater than the temperature of the other, and indicator means coupled to said first and second probes for providing indicia of the relative amplitude of said signals, wherein:
said first and second probes each include an electrode of a first thermally conductive material, a first conductor of a second material, a first thermopile including conductors of a second material and a third material, a second thermopile including conductors of said first and third materials;
said first conductor, first thermopile and second thermopile being electrically coupled to one another at junctions thermally coupled to said electrode to form first, second, and third thermoelectric junctions generating first, second and third thermoelectric potentials respectively,
and
a second conductor of said third material electrically coupled to said electrode;
first and second variable voltage divider means each for generating a signal indicative of a controlled fraction of the potential at its input terminal thereof;
third variable voltage divider means for generating at an output terminal thereof a signal indicative of a controlled fraction of the potential difference between first and second input terminals thereof;
first switch means for coupling said input terminal of said first variable voltage divider means to either said first conductor or to said first thermopile;
second switch means for coupling said input terminal of said second voltage divider to said conductor of said first material of said second thermopile or to said conductor of said third material of said second thermopile, said first and second switch means operating in synchronism such that in a first position said input terminals of said first and second variable voltage dividers are coupled respectively to said first conductor and said conductor of said first material of said second thermopile in a second position, said input terminals of said first and second variable voltage dividers are coupled respectively to said first thermopile and to said conductor of said third material of said second thermopile;

said input terminals of said third voltage divider means coupled to said output terminals of said first and second voltage divider means;

a resistor;

said second conductor being coupled through said resistor to said indicator means;

said first and second probe third voltage divider output terminals also being coupled to said indicator means, electrically coupling said probes in series opposition;

said apparatus further comprising means for adjusting said first and second probe first voltage divider means in synchronism;

means for adjusting said first and second probe second voltage divider means in synchronism; and means for adjusting said first and second probe third voltage divider means in synchronism.

* * * * *